United States Patent [19]

Agdanowski

[11] Patent Number: 4,488,548
[45] Date of Patent: Dec. 18, 1984

[54] ENDOTRACHEAL TUBE ASSEMBLY

[75] Inventor: Ronald T. Agdanowski, St. Peters, Mo.

[73] Assignee: Sherwood Medical Company, St. Louis, Mo.

[21] Appl. No.: 452,246

[22] Filed: Dec. 22, 1982

[51] Int. Cl.³ .............................. A61M 16/00
[52] U.S. Cl. .................. 128/204.25; 128/207.15
[58] Field of Search ............... 128/204.25, 207.15, 128/207.14, 200.26, 911, 207.16, 205.24

[56] References Cited

U.S. PATENT DOCUMENTS

| | | | |
|---|---|---|---|
| 3,402,717 | 9/1968 | Doherty | 128/207.15 |
| 3,683,908 | 8/1972 | Don Michael et al. | 128/207.15 |
| 3,771,527 | 11/1973 | Ruisi | |
| 3,788,326 | 1/1974 | Jacobs | 128/207.15 |
| 3,890,976 | 6/1975 | Bazell et al. | 128/207.15 |
| 4,007,737 | 2/1977 | Paluch | 128/911 |
| 4,265,237 | 5/1981 | Schwanbom et al. | 128/205.24 |
| 4,270,530 | 6/1981 | Baum et al. | 128/204.25 |
| 4,327,720 | 5/1982 | Bronson et al. | 128/207.15 |
| 4,416,273 | 11/1983 | Grimes | 128/207.15 |

FOREIGN PATENT DOCUMENTS

| | | | |
|---|---|---|---|
| 2366844 | 6/1978 | France | 128/207.15 |
| 2063686 | 6/1981 | United Kingdom | 128/204.25 |

OTHER PUBLICATIONS

"Bizzari-Giuffrida Endoesophageal Tube", 1959, Darol Catalogue.
Klain, "High Frequency Ventilation", Respiratory Care, May 1981, vol. 26, No. 5, pp. 427-429.
Klain et al., "High Frequency Jet Ventilation in CPR", Critical Care Medicine, May 1981, pp. 421-422.
Boysen, "High Frequency Ventilation", Respiratory Therapy, Sep./Oct. 1982, pp. 105-106.

*Primary Examiner*—Henry J. Recla
*Attorney, Agent, or Firm*—Stanley N. Garber; Gregory E. Upchurch; William R. O'Meara

[57] ABSTRACT

An endotracheal tube assembly is provided which includes an endotracheal tube, and an insufflation catheter connectable to a source of high frequency gas and disposed in the tube. The tube has spacers adjacent the distal end to space the distal end of the catheter from the inner sidewalls of the tube. The catheter may be provided with a ventilation lumen, a suction lumen, and connection means for supplying gas to the ventilation lumen and/or negative pressure to the suction lumen.

13 Claims, 5 Drawing Figures

U.S. Patent  Dec. 18, 1984  4,488,548
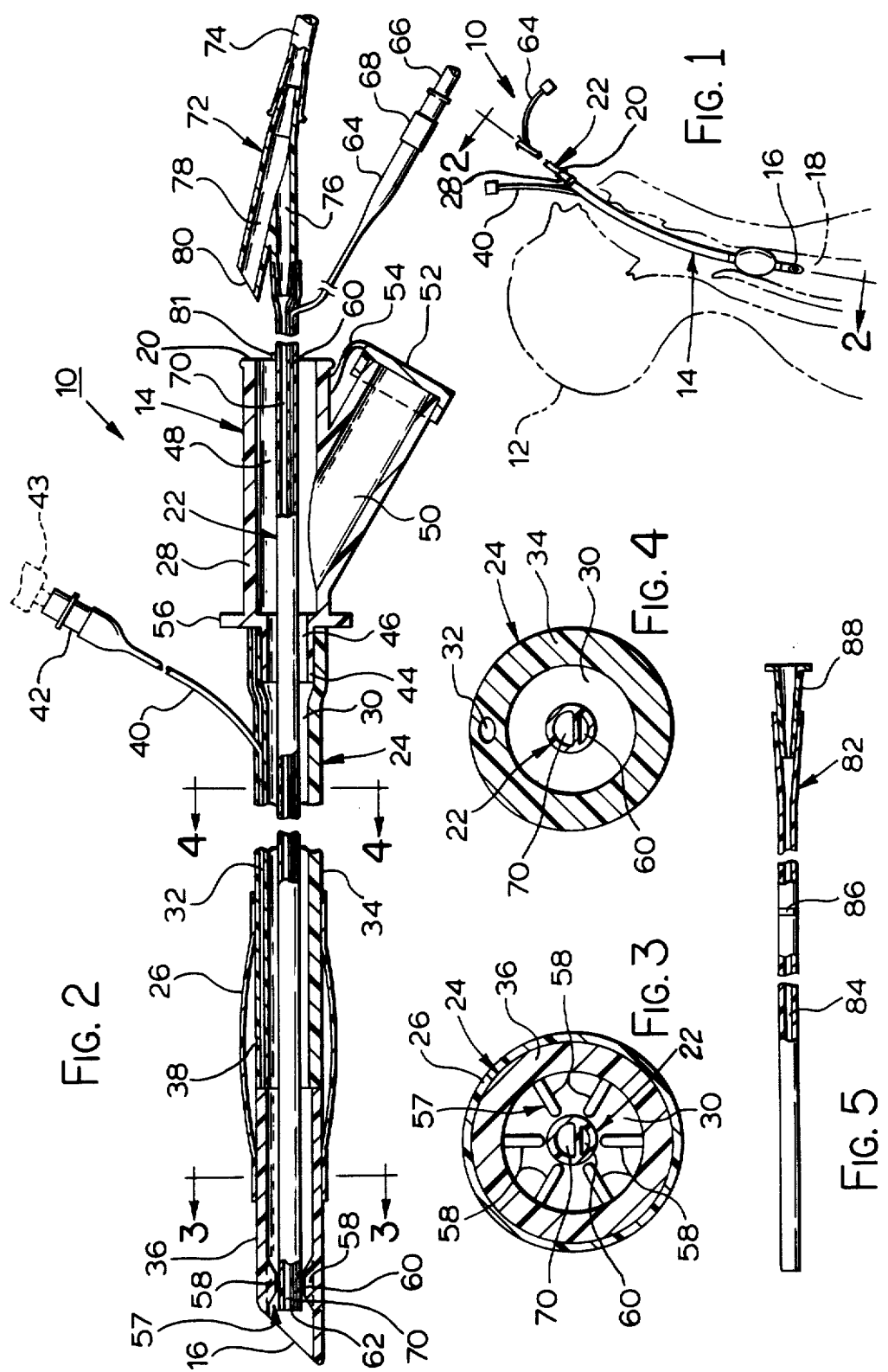

4,488,548

ENDOTRACHEAL TUBE ASSEMBLY

DESCRIPTION

1. Technical Field

This invention relates to endotracheal tube assemblies and, more particularly, to an endotracheal tube assembly capable of providing high frequency jet ventilation.

2. Background Art

As is well known, endotracheal tubes are inserted through the oral or nasal passage and into the trachea, and are generally provided with an expansible cuff or balloon which is expanded in the trachea to provide a seal between the trachea walls and the tube. These tubes are commonly used for conventional respiratory ventilation so as to perform the breathing function or assist the patient in breathing. Gas, such as oxygen and air, which may be humidified, is usually supplied in pulses at the normal breathing frequency which may be 20 pulses per minute.

In recent years, high frequency ventilation, referred to herein as "HFV", such as high frequency jet ventilation, referred to herein as "HFJV", has been under study and has had some use because it is believed to have certain substantial advantages over conventional ventilation. In HFJV, pulses of ventilation gas at a substantially higher velocity than that employed in conventional ventilation systems and at a frequency substantially greater than the normal breathing frequency, for example, at a rate of 50 to 500 per minute, are supplied to the trachea. Each pulse of gas effects a desirable entrainment of air and transports it to the lungs. Each pulse of gas or the entrained air may be humidified.

Some of the advantages of HFJV over conventional ventilation systems are believed to be improved gas diffusion, mobilization of secretions, and good gas exchange by the lungs even though there are relatively low tidal volumes of gas. It is believed that there is lower risk of pulmonary borotrauma and, also, that there is minimization of circulatory depression while maintaining adequate gas exchange.

In introducing such high frequency gas pulses, an insufflation tube or catheter of substantially smaller size than a conventional endotracheal tube may be inserted into an endotracheal tube that has been placed in the trachea of the patient, and the catheter then connected to a high frequency source of gas. Another method has been to employ an endotracheal tube having a longitudinally extending auxiliary lumen formed in the sidewall of the tube which connects with the main lumen of the tube a short distance from the distal or patient end of the tube.

There have been certain problems associated with applying HFJV to the patient. For example, when a high frequency jet ventilation or insufflation catheter is inserted into an endotracheal tube that has been placed in the trachea, the distal end of the catheter can lie against the sidewall of the endotracheal tube lumen or sidewall of the trachea, depending upon how the catheter is inserted. This reduces the ability of the gas pulses to entrain air thereby undesirably reducing the amount of air brought into the lungs. Also, the gas pulses cause the catheter, and especially the distal end, to whip or vibrate against the wall of the endotracheal tube or against the wall of the trachea thereby causing discomfort or even damage to the patient. Where an auxiliary lumen in the sidewall of the endotracheal tube is employed, the gas pulses are directed at an angle to the longitudinal axis of the endotracheal tube and this impedes air entrainment.

Since fluids, such as mucous, generally accumulate in the trachea while the endotracheal tube is in place, it is often necessary to use a suction catheter to clear the trachea of such fluids. This may be done by removing the insufflation catheter, where used, and inserting a suction catheter into the endotracheal tube, however, use of a separate suction catheter requires time to remove the insufflation tube and to insert the suction catheter into the endotracheal tube. This results in an extended period of time during which patient ventilation is stopped. Also, the separate suction catheter requires packaging, storage and, in general, higher costs. If a suction catheter is inserted into the endotracheal tube while the insufflation catheter is in the endotracheal tube, the insertion of the suction catheter may be hampered or difficult to accomplish. Furthermore, if both catheters are disposed in the endotracheal tube, the insufflation catheter may be displaced to a position where the entrainment of air and its desirable effects tend to be reduced.

SUMMARY OF THE INVENTION

It is therefore an object of the present invention to provide an improved endotracheal tube assembly capable of use in HFJV systems wherein good air entrainment, reduced vibration or whipping, and multipurpose capability are obtainable and which, in general, overcomes or reduces one or more of the above-mentioned problems of prior art devices.

In accordance with one aspect of the present invention, an endotracheal tube assembly is provided which includes an endotracheal tube, a catheter adapted for connection with a source of high frequency ventilation gas, and spacing means adjacent the distal end of the endotracheal tube to space the catheter from the sidewalls of the endotracheal tube.

These, as well as other objects and advantages of the present invention, will become apparent from the following detailed description and accompanying drawing.

BRIEF DESCRIPTION OF THE DRAWING

FIG. 1 is a diagramatic illustration of an endotracheal tube assembly in accordance with a preferred embodiment of the present invention with the assembly shown disposed in a patient;

FIG. 2 is a cross-sectional view, on an enlarged scale, taken along line 2—2 of FIG. 1;

FIG. 3 is a cross-sectional view, on an enlarged scale, taken along line 3—3 of FIG. 2;

FIG. 4 is a cross-sectional view, on an enlarged scale, taken along line 4—4 of FIG. 2; and FIG. 5 is a side view, partly in section and on a reduced scale, of a modified insufflation catheter capable of use in the endotracheal tube of FIG. 1.

DETAILED DESCRIPTION OF THE PREFERRED EMBODIMENT

Referring now to the drawing, and particularly to FIG. 1, an endotracheal tube assembly 10 is shown disposed in the natural airway of a patient that is indicated in phantom at 12. The assembly 10 includes a curved endotracheal tube 14 having a distal end 16 disposed in the trachea 18 of the patient, and a proximal end 20 externally of the patient. Disposed in the endotracheal tube 14 is an insufflation catheter 22 which is adapted to be connected to a high frequency gas source for effecting HFJV, as will be discussed hereafter.

As best seen in FIG. 2, endotracheal tube 14 includes a flexible tube 24 having a balloon or cuff 26 adjacent the distal end 16 and a "Y" connector 28 at the proximal end 20. Cuff 26 is shown as an inflatable or expansible cuff which may be of conventional design. Tube 24 has a main lumen 30 open at the distal and proximal ends, and an inflation lumen 32 extending longitudinally through the sidewall of the tube. Tube 24 includes a main tube section 34 of a suitable flexible material such as plastic or rubber, for example, it may be extruded from a plastic such as polyvinyl chloride or the like, and a distal end section 36 which may be, for example, molded of a flexible material, such as, for example, polyvinyl chloride or the like. The distal and proximal ends of tube sections 34 and 36, respectively, are secured together in aligned relation such as by a suitable cement, bonding agent or by other means. The end section 36 has solid walls and, in the illustration, closes the distal end of inflation lumen 32 which is formed in section 34 of the tube.

Cuff 26 extends axially across the abutting ends of the tube sections 34 and 36 with the distal and proximal ends of the cuff respectively connected to the two sections. A suitable cement, solvent or other means of connecting the ends of the cuff to the endotracheal tube in fluid-tight relation may be used. Cuff 26 may be formed of a suitable material such as a plastic, for example, polyvinyl chloride or polyurethane. An inflation port or sidewall opening 38 connects the interior of cuff 26 with the inflation lumen 32 at the distal end of the tube 24. Near the proximal end of the inflation lumen 32 is an inflation tube 40 which extends through a sidewall portion of tube 24 from the inflation lumen 32 to the exterior of the tube 24. The end of the inflation tube 40 may be provided with a one-way valve 42 which may be of any conventional design. Such valves, for example, may be of the type in which the tip end of a syringe, such as indicated in phantom at 43, is inserted into the valve and air pumped into tube 40, lumen 32, port 38, and the cuff 26 to inflate the cuff when desired. The valve 42 will allow air flow through it and into the cuff 26 when actuated to the open position by the tip of the syringe. The valve 42 may be biased to the closed position to maintain the cuff inflated when the syringe is removed. In some cases, instead of employing a valve, such as valve 42, a pinch clamp is used to open and close the inflation tube, such as tube 40.

The connector 28 is shown having a distal end portion 44 inserted into the proximal end of endotracheal tube 24 to form a fluid-tight connection. End portion 44 has a bore 46 which connects with main lumen 30 of tube 24 and a pair of bores 48 and 50 in connector 28. Bore 50 is shown closed at its proximal end by an end cap 52 integrally connected to the connector by an integral strap 54. Bore 48 is shown open at its proximal end to receive catheter 22. The connector 28 is also provided with a flange 56 which may be used to secure the device 10 to the patient.

The tube section 36 at the distal end of tube 24 is provided with catheter spacing means, indicated generally at 57, adjacent the distal end of tube 24 for spacing the distal end portion of catheter 22 from the sidewalls of lumen 30. As also seen in FIG. 3, the spacing means 57 is shown including a plurality of integral radially inwardly extending spacers or ribs 58. Spacers 58 are circumferentially equally spaced and extend inwardly toward the center or longitudinal axis of the tube 24. The space between adjacent ribs is less than the diameter of the catheter 22 so that the catheter will readily enter the center of the array of spacers 58 and be maintained spaced from the sidewalls of lumen 30 of tube 24. Since the spacers 58 are shown of equal radial extent, the catheter 22 is centered along the longitudinal axis of the tube 24 so that it is substantially equally spaced from the sidewalls of lumen 30.

Catheter 22 has an insufflation or gas ventilation lumen 60 open at the distal end 62 of the catheter and a proximal end connected with a connector tube 64 that passes through the sidewall of catheter 22 to the exterior of the catheter. Tube 64 is shown connected to a high frequency gas supply tube 66 through a suitable or conventional tube connector 68. Gas supply tube 66 is adapted to be connected to a high frequency gas source for supplying pulses of gas through the connector 68, tube 64, insufflation lumen 60, to effect gas pulses moving out the distal end opening of lumen 60. The distal end opening of lumen 60 acts as a jet for effecting pulses of gas at relatively high velocities in a distal direction toward the lungs (FIG. 1).

In the preferred embodiment, the catheter 22 also has a suction lumen 70 open at both distal and proximal ends. A suitable or conventional vacuum breaker or vacuum control device 72 is shown frictionally and sealingly connected to the proximal end of the catheter in communication with suction lumen 70. The proximal end of the vacuum control device 72 is connected to a vacuum line or tube 74 adapted to be connected to a suitable or conventional fluid collection container and a source of vacuum, such as the conventional hospital vacuum source. Control device 72 has a flow passage 76 connecting the suction lumen 70 with the tube 74, and a passage 78 having an inlet to the atmosphere at 80 and which connects with the passage 76. The thumb of a person may be placed over inlet 80 or partially over the inlet to control the flow of air from the atmosphere into the passage 76 to control the effective magnitude of negative pressure or vacuum in the suction lumen 70 during use of the device 10 when employed to suction fluid from the trachea.

The catheter 22 is substantially longer than the endotracheal tube 14 and is slidable into and out of tube 14. It is long enough to permit the distal end 62 to be substantially moved distally beyond tube 14 to permit the suctioning of fluids from the trachea as will be further discussed herein. Also, the catheter 22 is provided with indicia indicated at 81, for example, a printed marker, piece of tape, or the like, that can be used to properly position the catheter relative to tube 14 such as shown in FIG. 2. When indicia 81 is adjacent the proximal end of bore 48, the catheter is properly located.

While the catheter 22 is shown as a multi-purpose catheter having a jet ventilation lumen 60 and a suction lumen 70, a jet insufflation or ventilation catheter 82, such as shown in FIG. 5, and having only a single ventilation lumen 84, may be used in place of catheter 22 where desired. Also, if desired, catheter 22 can be removed through the proximal end of endotracheal tube 14 and the catheter 82 inserted into the endotracheal tube 14 until the distal end is positioned similar to the distal end of catheter 22 in FIG. 2, that is, with the distal end of tube 82 spaced from the inner sidewalls of lumen 30 by the radial spacers 58. A marker 86, for example, a painted band, may be predeterminately located on catheter 82 so that when the marker reaches the distal end of connector 28, the distal end of catheter 82 will be properly located in tube 24. In FIG. 5, the catheter 82 is shown having a luer-tapered tube connector 88 connected with the lumen 84 for connecting lumen 84 with a source of high frequency gas.

In using the endotracheal tube assembly 10 for the purpose of producing high frequency jet ventilation only for the patient 12 of FIG. 1, the endotracheal tube 14 with catheter 22 may be inserted in the conventional manner such as through the mouth and into the trachea as illustrated. After proper insertion, the endotracheal tube 14 is secured in place, for example, by taping an external portion of tube 24 to the face of the patient. The insufflation tube 22 may be secured in relation to endotracheal tube 14, for example, by taping it to connector 28. The cuff 26 may be inflated by introducing air into tube 40, for example, by means of syringe 43. A conventional pilot cuff or balloon (not shown) may be connected to tube 40 in communication with cuff 26 to provide an indication of the presence and amount of pressure in the cuff 26. As is well known, the inflated cuff 26 will space the distal end of tube 24 from the walls of the trachea and provide a seal between the trachea walls and tube 24 preventing any fluid flow between them. When device 10 is to be used for ventilation only, there is no need for the suction source to be connected to suction lumen 70 so that connector 72 and tube 74 need not be connected with tube 22 if desired.

With the connector 68 connected to gas supply tube 66 and a source of high frequency pulses of gas turned on so as to supply gas pulses to ventilation lumen 60, pulses of gas issue from the distal end of lumen 60. The source should have pressure capabilities to produce pulses of air from the distal end of lumen 60 that are of a velocity substantially greater than the velocity of pulses employed in conventional ventilation systems. The frequency of the gas supply pulses may be, for example, at a frequency of 200 pulses per minute. With the open end serving as a jet, pulses of gas at a relatively high velocity issue from the open distal end of lumen 60 and are directed toward the lungs of the patient 12. These high velocity pulses of air entrain air from the main lumen 30 which is open at the proximal end to the atmosphere. The gas pulses and entrained air move toward the lungs to produce good mixing of gas within the lungs and provide good ventilation for excellent gas exchange by the lungs.

Each gas pulse effects good air entrainment substantially from all sides of catheter 22 since the distal end of the catheter is spaced from the sidewalls of lumen 30 of the endotracheal tube 24 by spacers 58. The open end of the lumen 60 is substantially centered and air can readily flow axially past the end 62 of catheter 22 and spacers 58. Catheter 22 extends beyond the spacers 58 but the distal end 62 is proximal of the distal end 16 of the tube 24 so that there is less chance of having the distal end of lumen 60 closed by engagement with body tissue or of being closed by body matter. As will be apparent from FIG. 3, the sum of the cross-sectional areas of spacers 58 is substantially less than the cross-sectional area of the lumen 30 at the spacers so that they produce little air flow resistance and substantially do not impede air entrainment.

During HFJV, the array of spacers 58 not only centers catheter 22 for good air entrainment but also limits the movement of the distal end section of the catheter so that it cannot whip against the walls of lumen 30 as the pulses of gas are applied to lumen 60. The spacers, in limiting radial movement of the distal end of the catheter, reduce vibrations of the tube 14 during ventilation of the patient.

Where desired, conventional ventilation of the patient may be employed by connecting a source of ventilation gas which supplies pulses at a physiological frequency, for example, 20 cycles per minute, to the bore 50 instead of supplying HFJV gas to tube 64 and lumen 60 of catheter 22. Where conventional ventilation is to be used, the conventional source of gas may be connected to the distal end of bore 50 and the distal end of connector bore 48 closed (with or without catheter 22 in the endotracheal tube 14) to prevent short-circuiting of the gas to the atmosphere.

Where it is desired to change from conventional ventilation to HFJV, the conventional gas source may be disconnected from the endotracheal tube 14, the catheter 22 inserted into tube 14, if not present, and the connector 68 connected to tube 66 to connect a source of high frequency gas to lumen 60 of the catheter 22.

Where a multi-lumen catheter such as catheter 22 is employed and it is desired to remove accumulated fluids from the trachea by suctioning, the connector 72 and vacuum supply tube 74 may be connected to a vacuum or suction source, and the catheter 22 distally moved past the distal end of endotracheal tube 14 so that the catheter extends further into the trachea and fluids in the trachea can be moved into suction lumen 70. This suctioning will generally be done without the HFJV gas supplied to lumen 60. After the suctioning of fluid from the trachea has been accomplished, the catheter may be returned to its position as shown in FIG. 2 and HFJV continued. During suctioning, the vacuum control or vacuum breaker 72 may be employed in a conventional manner, that is, a finger may be placed or moved across the inlet 80 to vary the negative pressure in the suction lumen 70.

Various forms of spacers 58 may be employed to center the distal end portion of catheter 22 or 82 so that air from substantially all sides of the tube can be entrained during HFJV. In the drawing, the proximal ends of the spacers 58 are inclined distally and radially inwardly to serve as ramps for guiding the distal end 62 of the catheter 22 into the center of the array of spacers when the catheter is inserted into its shown position.

When it is desired to remove the endotracheal tube 14 from the patient, the valve 42 is actuated, such as by syringe 43, and air is removed from the cuff 26 to deflate it prior to removal.

The size or cross-sectional areas of the ventilation lumens, such as lumen 60 and 84 in the catheters illustrated, may vary in accordance with the size of the patient, pressure of the ventilation gas source, or physical condition of the patient. For example, the cross-sectional areas of these ventilation lumens may be between about 0.4 sq.mm. and 3 sq.mm. The cross-sectional area of the suction tube may be made large enough, for example, two to three times that of the ventilation lumen, to provide effective suctioning but not so large as to cause the catheter to undesirably impede air entrainment in an endotracheal tube of normal size. Endotracheal tubes, for an adult, may have, for example, an inner diameter of 7.5 mm. The catheter 22 is preferably a catheter extruded with the lumens 60 and 70 formed during extrusion and partitioned by the shown axially extending integral wall.

While the insufflation catheter 84 has been described in the preferred embodiment as slidable into and out of the endotracheal tube 14, in some cases, if desired, the insufflation catheter 22 may be secured in place in tube 14, such as by cementing the distal end of catheter 22 to the spacers 58.

As various changes could be made in the above construction without departing from the scope of the invention, it is intended that all matter contained in the above description or shown in the accompanying drawing shall be interpreted as illustrative and not in a limiting sense.

I claim:

1. An endotracheal tube assembly for effecting high frequency jet ventilation of a patient comprising an endotracheal tube having a tube lumen extending therethrough and a distal end for insertion into the trachea of a patient, and a proximal end adapted to be disposed externally of the patient when said distal end is in the trachea, a catheter slidably extending into said tube lumen and having a length such that the distal end thereof is located adjacent to said distal end of said tube and the proximal end thereof extends from the proximal end of said tube, said proximal end of said catheter including means adapted to be connected to a source of high frequency pulsating gas, said catheter being slidable relative to the entire length of said tube, and means integral with the distal end of the tube for maintaining said distal end of said catheter substantially centered within said tube.

2. The assembly of claim 1 wherein said integral means includes an array of circumferentially spaced ribs extending generally radially inwardly from the inner sidewall of said tracheal tube to limit movement of said distal end of said catheter during high frequency jet ventilation of a patient, the radial inner ends of said ribs being spaced from each other to provide a central space for receiving the catheter.

3. The assembly of claim 2 wherein each of said ribs extends axially within said tube and each has a proximal end wall inclined radially inwardly and distally whereby said distal end of said catheter engages and is guided into said central space of said array by at least one of said spacer ribs when said distal end is inserted into said array.

4. The assembly of claim 1 wherein said catheter includes a plurality of longitudinally extending lumens, and means for connecting the source of gas to the proximal end of one of said lumens, and means for connecting a source of suction to the proximal end of another of said lumens.

5. The assembly of claim 4 wherein said catheter is substantially longer than said tube so that the distal end thereof can be moved distally of the distal end of said tube.

6. The assembly of claim 5 further comprising a tube connector connected to the proximal end of said tube, said connector having a pair of fluid flow passages connected in fluid communication with said tube and a closure cap for selectively closing one of said passages, said catheter being insertable into one of said passages and into said tube.

7. The assembly of claim 1 wherein said tube includes distal and proximal tube sections connected together, and said spacer means is integral with said distal tube section.

8. The assembly of claim 1 wherein said catheter includes indicia means for providing an indication that said distal end of said catheter is spaced from the inner sidewalls of said tube by said spacer means and is proximally spaced from the distal end of said tube.

9. An endotracheal tube assembly for effecting high frequency jet ventilation of a patient comprising an endotracheal tube having a distal end for insertion into the trachea of a patient, a proximal end adapted to be disposed externally of the patient when said distal end is in the trachea, and a tube lumen extending therethrough from said proximal end to said distal end, an insufflation catheter slidably positioned in said tube lumen and having a ventilation lumen extending therethrough, said ventilation lumen having a distal end sized to provide a jet for effecting pulses of air therefrom and a proximal end including means adapted to be connected to a source of high frequency pulsating gas, said catheter having a length with respect to said tube lumen wherein the distal end thereof is located adjacent the distal end of said tube and the proximal end thereof extends from the proximal end of said tube, and spacer means within said lumen adjacent the distal end of said tube for locating the distal end of said catheter in spaced relation from the sidewalls of said tube lumen when the distal end of catheter is adjacent the distal end of said tube.

10. The assembly of claim 9 wherein said spacer means includes a plurality of integral, radially inwardly extending, circumferentially spaced ribs in a distal end section of said tube, said ribs substantially centering said catheter and limiting radial movement of said end section during use of the assembly.

11. The assembly of claim 10 wherein said tube includes a proximal tube section, and wherein said distal end section is a separate member secured to said proximal tube section, and further including an expansible cuff on said tube, and an inflation lumen for inflating and deflating said cuff.

12. The assembly of claim 10 wherein the sum of cross-sectional areas of said ribs is substantially less than the cross-sectional area of said tube.

13. The assembly of claim 10 wherein said catheter includes a suction lumen having a cross-sectional area greater than that of said ventilation lumen, said cross-sectional area of said ventilation lumen being between about 0.4 sq.mm. and 3 sq.mm.

* * * * *